United States Patent [19]

Summers et al.

[11] Patent Number: 5,772,668
[45] Date of Patent: Jun. 30, 1998

[54] APPARATUS FOR PLACING AN ENDOPROSTHESIS

[75] Inventors: David Paul Summers, Montgomery; Gary R. Ball, Spring, both of Tex.

[73] Assignee: American BioMed, Inc., The Woodlands, Tex.

[21] Appl. No.: 472,521

[22] Filed: Jun. 7, 1995

Related U.S. Application Data

[63] Continuation-in-part of Ser. No. 367,239, filed as PCT/US93/05823 Jun. 16, 1993, Pat. No. 5,607,445, which is a continuation-in-part of Ser. No. 900,896, Jun. 18, 1992, Pat. No. 5,342,387.

[51] Int. Cl.$^6$ ........................................................ A61F 2/06
[52] U.S. Cl. ............................................ 606/108; 606/191
[58] Field of Search ................................... 606/108, 198, 606/191, 195; 623/1, 12

[56] References Cited

U.S. PATENT DOCUMENTS

| | | | |
|---|---|---|---|
| 3,842,441 | 10/1974 | Kaiser | 3/1 |
| 3,868,956 | 3/1975 | Alfidi et al. | 128/345 |
| 4,503,569 | 3/1985 | Dotter | 3/1 |
| 4,512,338 | 4/1985 | Balko et al. | 128/1 R |
| 4,553,545 | 11/1985 | Maass et al. | 128/341 |
| 4,562,596 | 1/1986 | Kornberg | 623/1 |
| 4,580,568 | 4/1986 | Gianturco | 128/345 |
| 4,649,922 | 3/1987 | Wiktor | 128/343 |
| 4,733,665 | 3/1988 | Palmaz | 128/343 |
| 4,739,762 | 4/1988 | Palmaz | 128/343 |
| 4,740,207 | 4/1988 | Kreamer | 623/1 |
| 4,768,507 | 9/1988 | Fischell et al. | 128/303 |
| 4,800,882 | 1/1989 | Gianturco | 128/343 |
| 4,856,516 | 8/1989 | Hillstead | 128/343 |
| 4,878,906 | 11/1989 | Lindemann et al. | 623/1 |
| 4,886,062 | 12/1989 | Wiktor | 128/343 |
| 4,913,141 | 4/1990 | Hillstead | 606/108 |
| 4,950,227 | 8/1990 | Savin et al. | 604/8 |

(List continued on next page.)

FOREIGN PATENT DOCUMENTS

| | | | |
|---|---|---|---|
| 0380666 | 8/1980 | European Pat. Off. | A61L 31/00 |
| 0183372 | 6/1986 | European Pat. Off. | A61M 29/00 |
| 0282175 | 9/1988 | European Pat. Off. | A61F 2/06 |
| 0417928 | 3/1991 | European Pat. Off. | A61M 29/00 |
| 2678508 | 1/1993 | France | A61F 2/06 |

OTHER PUBLICATIONS

American Rioentgen Ray Society; *Expandable Intrahepatic Portacaval Shunt Stents: Early Experience in the Dog*; Julio C. Palmaz, M.D., et al; Oct. 1985; 5 pgs.

Radiology; Atherosclerotic Rabbit Aortas: Expandable Intraluminal Grafting; Julio C. Palmaz, M.D., et al; 1986; pp. 160:723–726.

Radiology; Expandable Intraluminal Vascular Graft: A Feasibility Study; Julio C. Palmaz, M.D., et al; Apr., 1985; 4 pgs.

Radiology; Expandable Intraluminal Graft: A Preliminary Study; Julio C. Palmaz, M.D., et al; 1985; pp. 156;73–77.

Technical Developments and Instrumentation; Transluminal Expandable Nitinol Coil Stent Grafting: Preliminary Report; Charles T. Dotter, M.D., et al; Apr. 1983; 2 pgs.

Radiology; Radiological Follow–up of Transluminally Inserted Vascular Endoprostheses: An Experimental Study Using Expanding Spirals; D. Maas, et al; pp. 659–663.

*Primary Examiner*—Michael H. Thaler
*Attorney, Agent, or Firm*—Conley, Rose & Tayon, P.C.

[57] ABSTRACT

An endoprosthesis or stent comprising a continuous loop of material is disclosed, along with a method and systems for deploying the stent at a desired location within a collapsed vessel. The stent can comprise a double spiral configuration or a double helix configuration, and can be coated with a slippery biocompatable substance. The systems for deploying a stent include catheters capable of maintaining a stent in a reduced diameter state and releasing the stent so that it can resume it expanded diameter state at the implantation site.

11 Claims, 5 Drawing Sheets

U.S. PATENT DOCUMENTS

| | | | |
|---|---|---|---|
| 4,954,126 | 9/1990 | Wallstén | 600/36 |
| 4,969,458 | 11/1990 | Wiktor | 606/194 |
| 5,041,126 | 8/1991 | Gianturco | 606/195 |
| 5,133,732 | 7/1992 | Wiktor | 606/195 |
| 5,147,370 | 9/1992 | McNamara et al. | 606/108 |
| 5,161,547 | 11/1992 | Tower | 128/898 |
| 5,306,294 | 4/1994 | Winston et al. | 623/1 |
| 5,370,691 | 12/1994 | Samson | 623/12 |
| 5,372,600 | 12/1994 | Beyar et al. | 606/108 |
| 5,514,176 | 5/1996 | Bosley | 606/191 X |

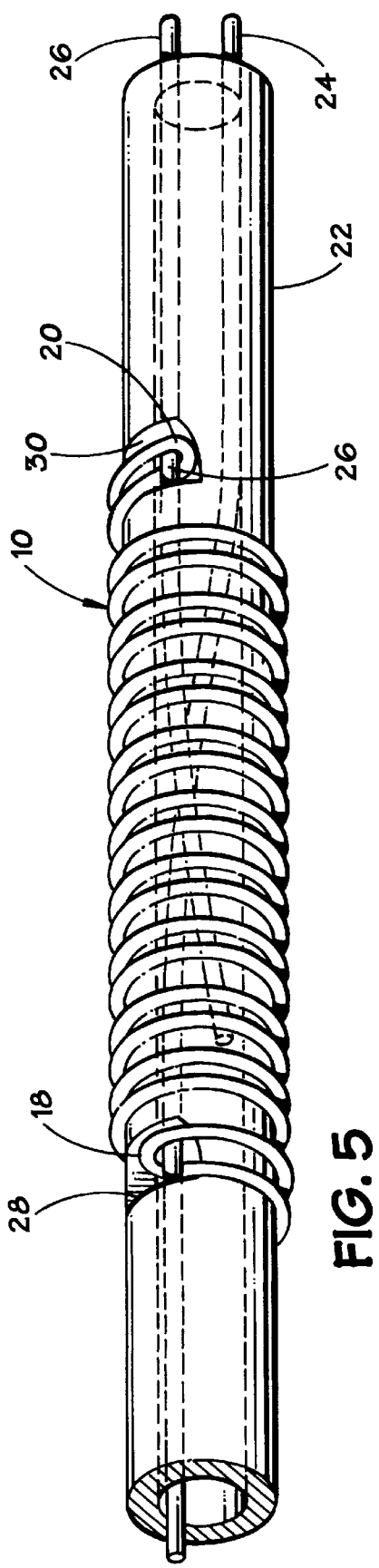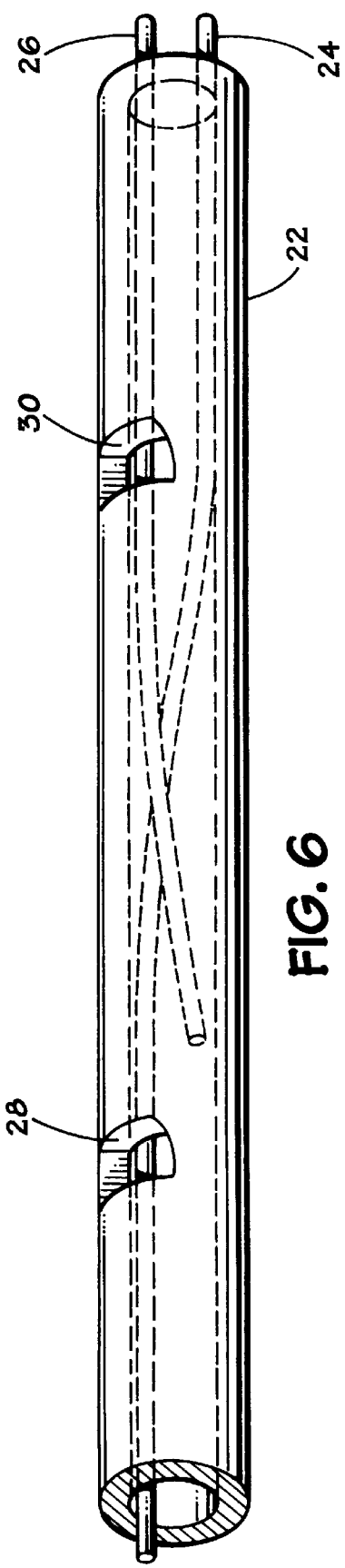
FIG. 5
FIG. 6

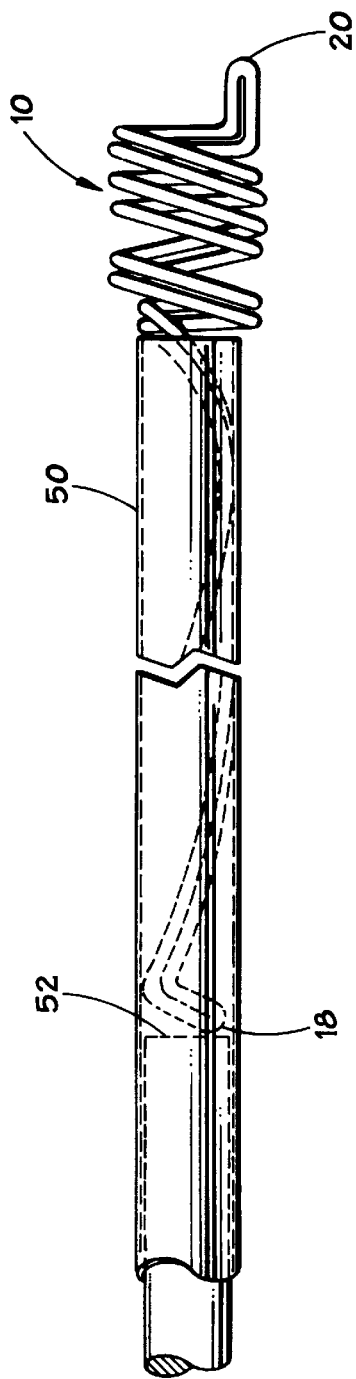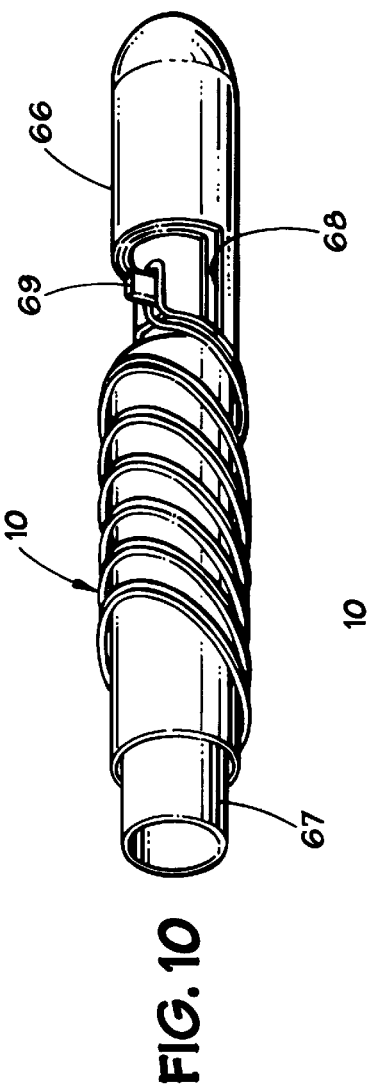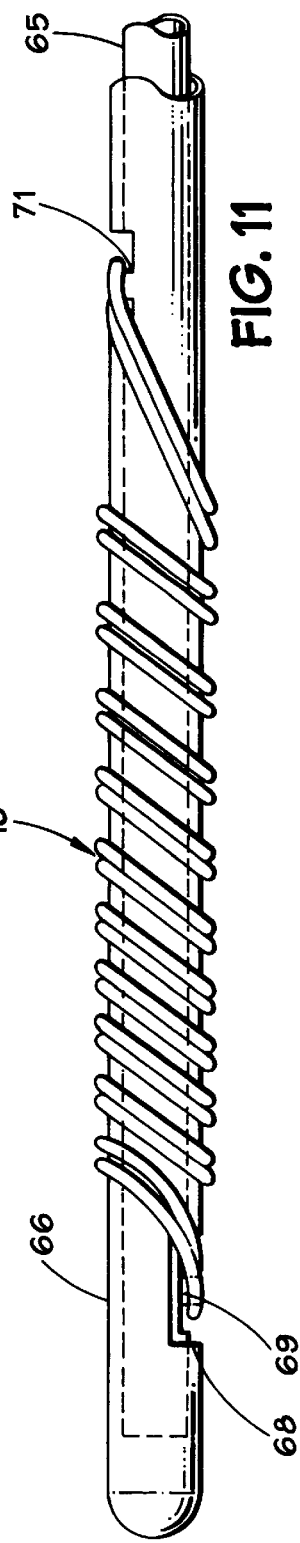

APPARATUS FOR PLACING AN ENDOPROSTHESIS

The present invention is a continuation-in-part of a copending application entitled "Method and Apparatus for Making a Stent," filed Dec. 16, 1994 claiming an international priority date of Jun. 16, 1993 (PCT No. PCT/US93/05823) and having Ser. No. 08/367,239, now U.S. Pat. No. 5,607,445 which is in turn a continuation-in-part of an application entitled "Artificial Support for a Blood Vessel," filed Jun. 18, 1992 and now issued as U.S. Pat. No. 5,342,387, each of which is incorporated herein in its entirety by reference.

TECHNICAL FIELD OF THE INVENTION

The present invention relates to supports for collapsed or occluded blood vessels or lumens, and more particularly, to methods for deploying a coiled wire stent for insertion and expansion in a collapsed or occluded blood vessel or lumen. The present invention further relates to systems and methods for manipulating artificial supports for blood vessels and, more particularly, to systems and methods for delivering a wire coil having certain desired properties to a desired site. Still more particularly, the present invention discloses methods and apparatus for delivering and deploying a reduced diameter stent to a particular site in a vessel or lumen and expanding the stent to an expanded diameter state.

BACKGROUND OF THE INVENTION

A typical wire stent for insertion and expansion in a collapsed or occluded blood vessel is shown in U.S. Pat. No. 4,800,882 and includes a coiled wire having a plurality of curved sections that are formed into a generally circular configuration. Adjacent curved sections are joined by a bend so that a series of alternating opposing loops are formed. The stent has a cylindrical shape with a longitudinal opening through which a folded balloon catheter is inserted. The opposing loops are tightly contracted about the catheter so that the cylindrical shape has an overlapping region in which portions of adjacent loops circumferentially overlap. The loops are arranged so that when the balloon catheter is inflated, adjacent loops diverge circumferentially relative to each other, thereby decreasing the width of the overlapping region while increasing the diameter of the cylindrical shape.

In operation, the stent is deployed at its desired position within the vessel in its reduced diameter state and the balloon is then expanded, forcing the stent to attain to its expanded state. As the diameter of the cylindrical stent increases, the stent engages the inner surface of the blood vessel for supportive engagement with the vessel wall.

Other stents are known in the art. For example, U.S. Pat. Nos. 5,041,126, 4,733,665, 4,649,922, 5,133,732 and 5,314,444 all disclose variations of the balloon-expandable stent. U.S. Pat. Nos. 4,580,560 and 4,554,545 disclose various spring loaded stents, and U.S. Pat. Nos. 4,503,569 and 4,512,338 disclose stents that rely on a memory metal to achieve the transition from compressed to expanded state.

The prior art stents have several deficiencies. As shown in FIG. 7 of U.S. Pat. No. 4,800,882, the alternating bends are aligned in relation to the longitudinal axis of the stent such that upon expansion of the stent as shown in FIG. 8, the opposing loops may be expanded such that a longitudinal gap appears between the opposing bends of the loops, leaving a longitudinal unsupported area along the occluded blood vessel. Such an unsupported area is undesirable.

Similarly, the balloon catheter is itself undesirable as an expansion means, as it may be subject to rupture, over-inflation, leakage, or even complete detachment and loss. For obvious reasons, it is desirable to avoid situations in which the balloon catheter or portions thereof become detached from the device.

Additionally, the stents of the prior art often require the application of heat or torsional force in order to attain their expanded state. All of these expansion methods can have adverse consequences if not applied precisely and correctly. Hence it is desired to provide a stent that can be quickly, easily and accurately deployed without the use of a balloon, or other expansion means that may be subject to failure or vulnerable to human error.

SUMMARY OF THE INVENTION

The stent of the present invention is radially expandable without the use of a balloon or the application of heat or torsional forces, and is constructed to provide a region of uniform support to a vessel wall. The present invention further comprises a two-part catheter adapted to receive and maintain the stent in a reduced-diameter state, and to release the stent at the desired location, allowing it to resume its expanded shape. The preferred embodiment of the present invention comprises a double spiral stent formed from an endless loop or ribbon that can be mounted on or in a deploying device and retained while the stent is maneuvered into the desired position. The present invention further discloses several deploying devices and methods of use thereof and discloses a coated double-spiral stent that may comprise either a single coil or a bifurcated coil.

Other objects and advantages of the present invention will appear from the following description.

BRIEF DESCRIPTION OF THE DRAWINGS

For a detailed description of a preferred embodiment of the invention, reference will now be made to the accompanying drawings wherein:

FIG. 5 is a perspective view of a first embodiment of the present stent delivery system with the stent of FIG. 1 positioned thereon, as it would appear prior to deployment in a vessel;

FIG. 6 is a perspective view of the stent delivery system of FIG. 5, with the stent removed therefrom;

FIG. 9 is a side view of a third stent delivery system, showing the stent in the process of being deployed;

FIG. 10 is a perspective view of a fourth stent delivery system, showing the stent coiled around the deployment device and ready for implantation;

FIG. 11 is a side view, partially in phantom, of the system of FIG. 10; and

DETAILED DESCRIPTION OF A PREFERRED EMBODIMENT

Figure 1:
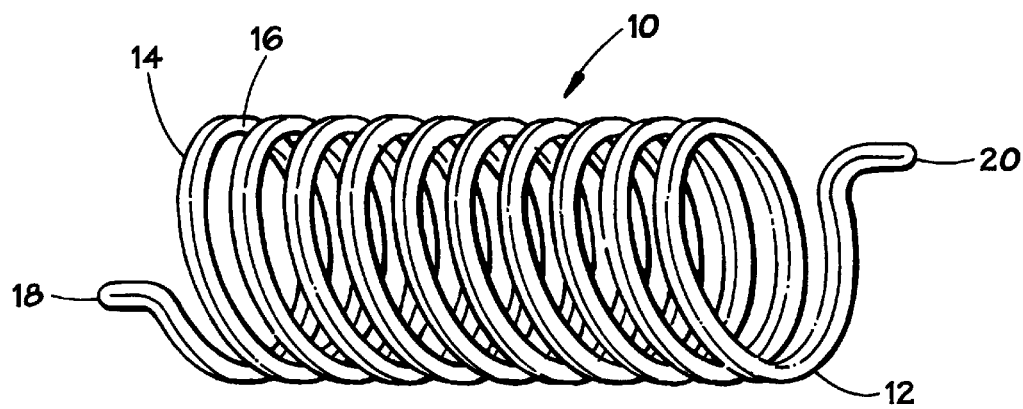
FIG. 1 is a perspective view of a double spiral stent according to the present invention.
Figure 2:
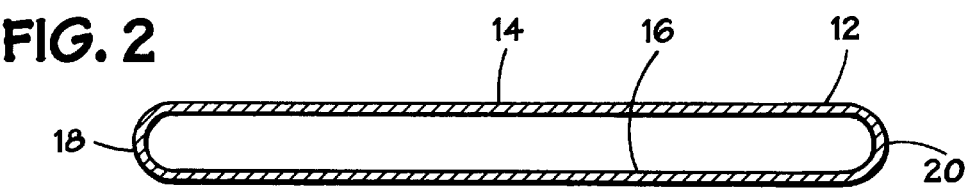
FIG. 2 is a plan view of a continuous loop of material that can be formed into the double-spiral stent of FIG. 1.

Referring initially to FIGS. 1 and 2, the double spiral stent 10 of the present invention comprises a coil formed from a continuous loop 12 having a pair of legs 14, 16 and a pair of end cusps 18, 20. Loop 12 is preferably wound into a continuous double-spiral having an even pitch such that legs 14, 16 provide uniform support for a vessel wall when the stent is in its expanded state. Stent 10 is preferably formed from a shape memory metal such as nitinol, or from a biocompatible material having a high index of elasticity. Stent 10 is constructed so that it can be temporarily formed into an alternative straight or coiled shape having a reduced diameter, deployed in a constricted blood vessel or other lumen while in this reduced diameter state, and then returned to its original, expanded diameter state. The continuous loop 12 from which stent 10 is formed can be manufactured by any of several methods, including etching or die-cutting the loop from a sheet of material, slicing a thin ring from a thin-walled tube of material, or forming the loop from a length of wire or metal ribbon by joining the ends in a permanent manner, such as by welding, and finishing the join so that a smooth and continuous surface is provided. The present invention relates particularly to means for deploying such a stent as discussed in the following paragraphs.

Alternatively, or in addition, the outside of stent 10 may also be coated with a slippery, biocompatible substance. In addition to having a low coefficient of friction, such substance may have other desirable properties including hydrophobicity, hydrophilicity, permeability and/or impermeability.

Figure 3:
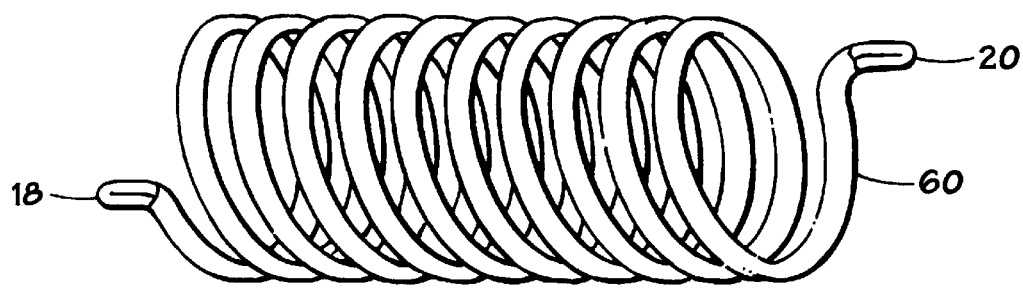
FIGS. 3 and 4 are side views of the stent of FIG. 1, fully and partially coated with a biocompatible deployment-facilitating layer, respectively.
Figure 4:
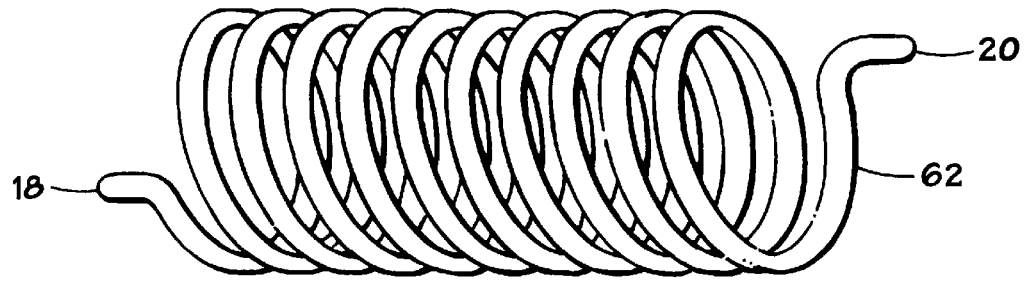

Referring now to FIG. 3, the sheath may comprise a sleeve 60 that does not enclose cusps 18, 20 of stent 10 but merely covers the parallel legs 14, 16 along their helical length. Alternatively, as shown in FIG. 4, such a coating may comprise a sheath 62 that completely encloses both legs and the cusps of stent 10. According to still another embodiment, the sheath may be applied individually to legs 14, 16 and to the entire length of the loop 12 that forms stent 10, so that the coated stent appears substantially as shown in FIG. 1. According to one embodiment, it is preferred that the sheath be thick enough to form a substantially unbroken wall between adjacent sheathed loops when the stent is in its expanded state.

Such a coating, sheath, or graft as it may be called, may comprise a tube-shaped member having an inside diameter only slightly larger than the circumference of the deployed stent. The graft may be made of latex, silicone latex, polytetraflouroethylene, polyethylene, dacron polyesters, polyurethane, living tissue such as a patient's autograft, dead tissue such as acellular vascular prosthesis (as described by Wilson, G. J. et al., *Trans.Am.Soc.Internal Organs*, Vol. XXXVI, 1990), or other suitable biocompatible material. The graft material must be flexible and durable, so that it can withstand the effects of installation and usage. Depending on the material chosen, it may be preferable to form the graft in one of several ways. For example, the graft may be extruded, woven or formed by dipping a substrate in the desired material, removing the material from the substrate, and trimming the end of the material, so as to form a cylindrical tube having an opening at each end. Examples of additional suitable coatings include polyester dacron, which is permeable, or polytetraflouroethylene, which is impermeable.

Referring now to FIGS. 5 and 6, a first device for deploying a double spiral stent comprises a hollow tube catheter 22 containing a pair of wires 24, 26. Tube 22 includes a pair of windows 28, 30, which are axially spaced along the length of tube 22 and communicate between the interior and exterior of the tube. The distance between openings 28, 30 is approximately equal to the desired length of the contracted stent. As shown in FIGS. 3 and 4, one end cusp 18 of stent 10 is partially inserted through opening 28 and one of the wires 24 is passed through the loop formed by cusp 18, thereby anchoring one end of stent 10 with respect to tube 22. Stent 10 is then tightly coiled around the outside of tube 22 between openings 28, 30 so that it is in direct contact with the outside of tube 22. At its second end, cusp 20 is partially inserted into opening 30, and the second wire 26 is passed through the loop formed by cusp 30, thereby anchoring the second end of stent 10 with respect to tube 22. The outside diameter of tube 22 is preferably such that when stent 10 is wound around tube 22, the total outside diameter of the stent and tube is small enough to be easily inserted into the constricted portion of a collapsed or constricted blood vessel.

Once the tightly coiled stent 10 has been positioned at the desired implantation site by insertion of tube 22, wires 24, 26 are withdrawn through tube 22 without removing tube 22, so that the end cusps 18, 20 of stent 10 are released. Wires 24, 26 can be withdrawn independently or simultaneously. In either case, when the ends of stent 10 are released, stent 10 immediately begins to return to its expanded diameter state. This is typically accomplished by the relative rotation of cusps 18, 20 as stent 10 uncoils, resulting in a stent having fewer complete turns but a larger diameter. The material from which stent 10 is constructed is preferably selected so that the full expansion of stent 10 is not rapid, but takes several seconds, or even minutes, in order to avoid applying sudden stresses to the vessel wall. Tube 22 may be constructed of any suitable material, namely one having sufficient rigidity to traverse the inner passageways of the body, and sufficient flexibility to do so without puncturing the vessel wall.

Figure 7:
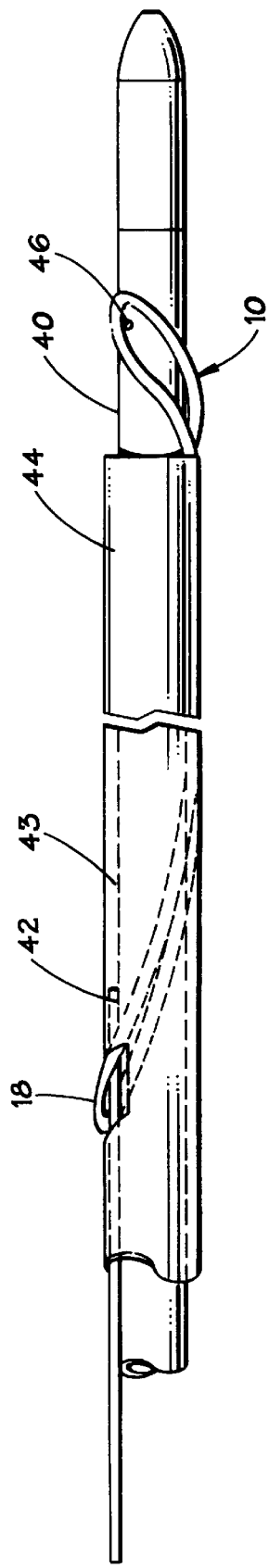
FIG. 7 is a side view of a second stent delivery system, as it would appear prior to deployment in a vessel.
Figure 8:
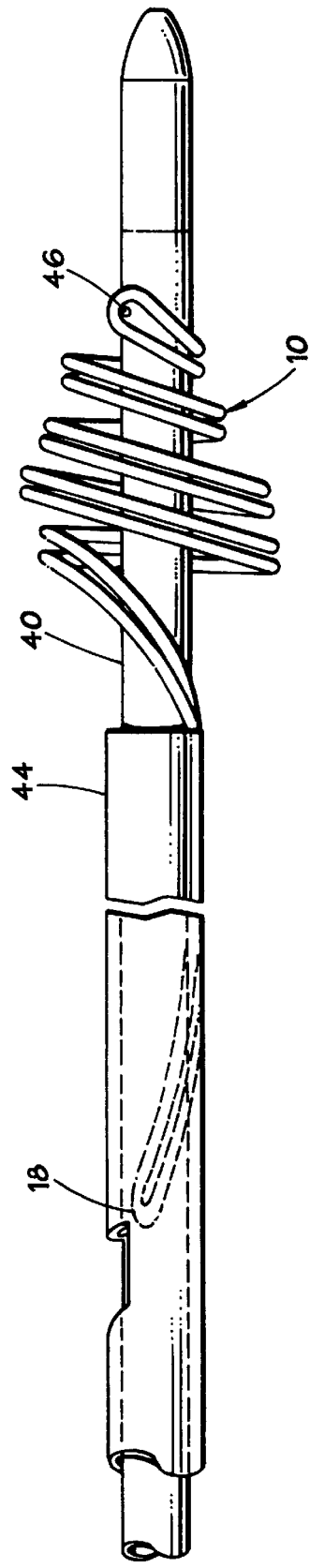
FIG. 8 is a side view of the system of FIG. 7, showing the stent in the process of being deployed.

Referring now to FIGS. 7 and 8, an alternative method for deploying stent 10 comprises wrapping it around an inner mandrel 40 and maintaining it in its wrapped state by means of a retaining wire 42 and an outer sheath 44. The inner surface of outer sheath 44 preferably has a slightly greater in diameter than the diameter of inner mandrel 40, so that a small annular clearance 43 is provided therebetween. Stent 10 is housed in this clearance during deployment. The forward end of stent 10 is hooked onto a small protrusion or pin 46 adjacent the forward end of mandrel 40. The rearward end of stent 10 passes around retaining wire 42. In this manner, the ends of stent 10 are fixed and cannot rotate or move relative to mandrel 40. The catheter comprising mandrel 40 and outer sheath 44 is positioned at the desired stent deployment site. To remove stent from the device, retaining wire 42 is withdrawn, releasing the rearward end of stent 10 and sheath 44 is gradually drawn back along mandrel 40 so that additional portions of stent 10 are released from confinement within sheath 44. As it is released from sheath 44, stent 10 tends to resume its expanded state, as shown in FIG. 8. Once sheath 44 is fully removed from stent 10, and stent 10 has attained its expanded state, mandrel 40 is easily disengaged from the forward end of stent 10 and withdrawn as described above.

Referring now to FIG. 9, still another method for deploying stent 10 is to elongate it until its diameter is sufficiently reduced to fit inside the inside diameter of a catheter tube 50. Stent 10 is maintained in a reduced diameter state by confinement in catheter tube 50 until it is pushed from tube 50. As stent 10 is pushed out of tube 50, it is no longer restrained and resumes its expanded diameter state. An ejector 52 having an outer diameter approximately equal to the inside diameter of tube 50 is used to apply an axial force to the proximal end 18 of stent 10, thereby causing it to be pushed from tube 50. Tube 50 is preferably lined with a slippery biocompatible substance having a low coefficient of friction, which facilitates the removal of stent 10 from the inside of tube 50.

Referring now to FIGS. 10 and 11, a fourth system for implanting a stent 10 comprises a catheter sheath 66 housing a rotatable mandrill 67. Sheath 66 includes a window 68 therethrough, and mandrill 67 includes a cam 69 that extends radial through window 68. Window 68 and cam 69 are positioned adjacent the forward end of catheter sheath 66. Sheath 66 may include a finger 71 positioned rearwardly of cam 69, or, in an alternative embodiment (not shown), may include a second window, through which a second cam extends from mandrill 67. A stent 10 is tightly wrapped around the exterior of sheath 66 and restrained at its ends by cam 69 and finger 71. In this manner, stent 10 is held in a reduced diameter state for implantation in a vessel.

Figure 12:
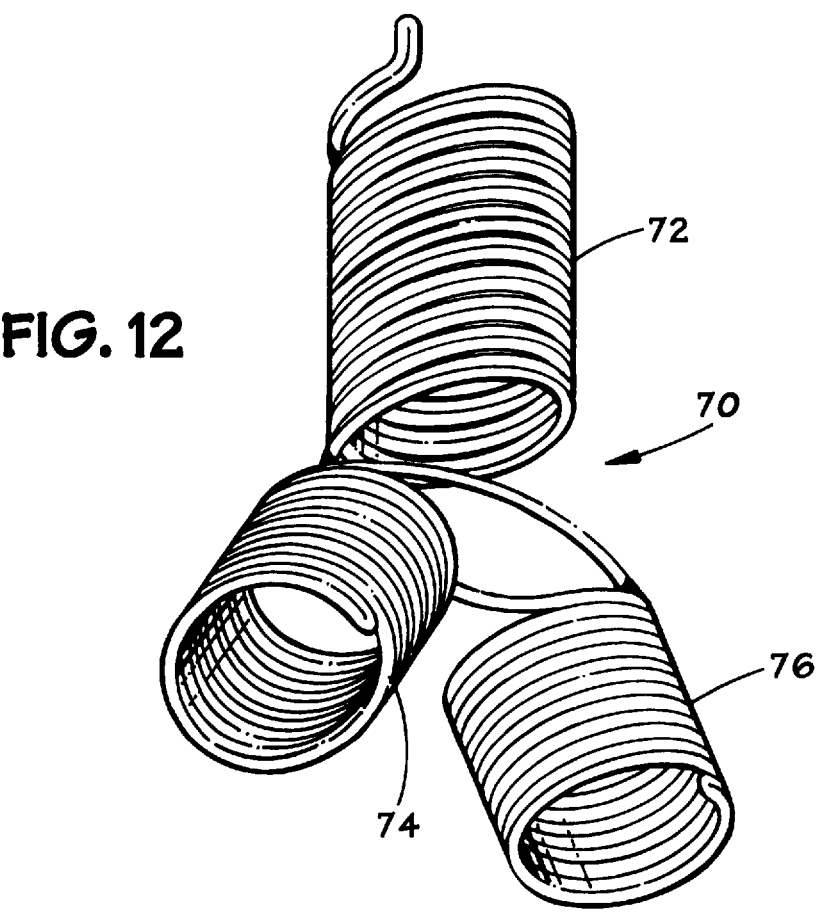
FIG. 12 is a perspective view of a bifurcated double-spiral stent according to the present invention.

Referring now to FIG. 12, an alternative embodiment of the present double spiral stent comprises a bifurcated double spiral stent 70 including a major coil 72 and minor coils 74, 76. Stent 70 may be coated individually or uncoated as shown in FIG. 12, or may be coated with a sheathing layer, as described above with respect to FIGS. 3 and 4. In either case, bifurcated stent 70 is formed from a continuous loop having no ends and which does not cross itself at any point.

Figure 13:
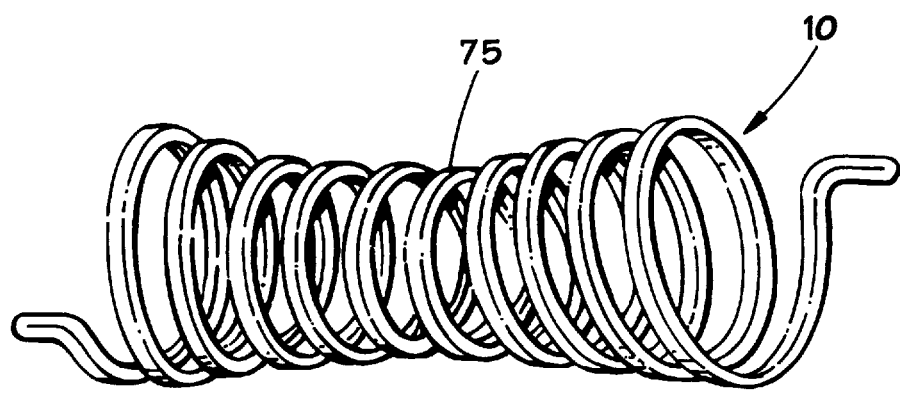

Referring now to FIG. 13, still another embodiment of the double-spiral stent comprises an hour-glass shaped stent 10 having a reduced diameter portion 75 between its ends. It has been found that the properties of blood and vessel tissue growth are such that robust myointamal hyperplasia that is stimulated by the placement of a stent within a vessel causes restenosis adjacent the ends of the stent. The restenosis process usually slows or stops within six months of implantation. This overgrowth of cells reduces the lumen diameter adjacent the ends of the stent. Therefore, it may sometimes be preferred to increase the diameter of the ends of the stent so that the passage through the stent remains clear and uniform even when cell growth has built up at the ends. FIG. 13 shows the stent having a relatively short middle portion, but it will be understood that the middle, reduced-diameter portion could be extended to any desired length, with the expanded diameter portions limited to the vicinity of the ends.

Because the stent of the present invention can be constructed from a continuous loop of wire, it eliminates the wire ends that are commonly present on the stents of the prior art. The present spiral stent also does not cross itself at any point, thereby providing a flush inner surface that allows substantially laminar flow and minimizes the likelihood of clotting that results when blood flow is too turbulent at a particular point.

When a stent according to the present invention is coated with a suitable biocompatible substance as described above, it can be used as a graft to seal an aneurysm or similar defect in a vessel. Prior to deployment, the stent is placed in the coating and collapsed. The graft may then be deployed and expanded by any of the means described above. The tissue of the vessel adjacent to the graft may grow onto the graft, reinforcing that part of the vessel wall and helping to reduce the risk of future ruptures at that location.

While a preferred embodiment of the invention has been shown and described, modifications thereof can be made by one skilled in the art without departing from the spirit of the invention. It will further be understood that stents according to the present invention may be used in other body passageways, such as the urinary, biliary, or esophageal tract, with construction and deployment of the stents being essentially as described above.

What is claimed is:

1. A system for deploying a stent, comprising:
a tube having at least two windows therethrough, said windows being spaced a distance apart along said tube;
at least one anchor wire extending through said tube;
a stent wrapped around said tube and extending between said windows, said stent comprising an endless loop of material having a pair of separate legs that are connected by a pair of end cusps, each of said cusps extending through one of said windows and engaging an anchor wire within said tube such that when said anchor wire is withdrawn through said tube said anchor wire releases said cusp.

2. The system according to claim 1 wherein said stent forms a coil having a first diameter when it is not restrained, said stent being held at a second, smaller diameter when it is restrained on said tube.

3. The system according to claim 2 wherein said stent returns to said first diameter when it is released from said tube.

4. The system according to claim 1, further including a second wire extending through said tube, each of said wires engaging one of said cusps.

5. The system according to claim 1 wherein said stent is encapsulated in a tubular coating so as to form a substantially unbroken wall when said stent is in its expanded state.

6. The system according to claim 1 wherein said stent is constructed of a superelastic metal.

7. The system according to claim 1 wherein said stent has a larger diameter adjacent its ends and a reduced diameter between its ends.

8. A system for deploying a stent, comprising:
a cylindrical support device supporting first and second retainers axially spaced apart thereon;
a stent comprising an endless loop of material, said stent wrapped around said support device and extending between said retainers, said endless loop comprising a pair of separate legs connected by a pair of cusps, each of said cusps engaging one of said retainers, the engagement of said cusps with said retainers maintaining said stent in wrapped relationship to said device such that when said retainers are disengaged from said stent, said cusps are released and said stent is thereby released from said device.

9. The system according to claim 8 wherein said stent is encapsulated in a tubular coating so as to form a substantially unbroken wall when said stent is in its expanded state.

10. The system according to claim 8 wherein said stent is constructed of a superelastic metal.

11. The system according to claim 8 wherein said stent comprises a double spiral coil formed from an endless loop of material.

* * * * *